United States Patent
Geyer et al.

(10) Patent No.: US 10,478,809 B2
(45) Date of Patent: Nov. 19, 2019

(54) CATALYST SYSTEM AND PROCESS FOR THE PRODUCTION OF GLYCOLS

(71) Applicant: SHELL OIL COMPANY, Houston, TX (US)

(72) Inventors: Reinhard Geyer, Leuna (DE); Henri Preising, Leuna (DE); Dionysius Jacobus Maria De Vlieger, Amsterdam (NL); Smita Edulji, Houston, TX (US); Evert Van Der Heide, Amsterdam (NL); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/777,096

(22) PCT Filed: Nov. 17, 2016

(86) PCT No.: PCT/EP2016/078079
§ 371 (c)(1),
(2) Date: May 17, 2018

(87) PCT Pub. No.: WO2017/085229
PCT Pub. Date: May 26, 2017

(65) Prior Publication Data
US 2018/0345256 A1    Dec. 6, 2018

(30) Foreign Application Priority Data
Nov. 19, 2015  (EP) .................................... 15195497

(51) Int. Cl.
| | | |
|---|---|---|
| *B01J 27/00* | (2006.01) | |
| *B01J 25/00* | (2006.01) | |
| *C07C 29/00* | (2006.01) | |
| *C07C 31/00* | (2006.01) | |
| *B01J 27/188* | (2006.01) | |
| *B01J 35/00* | (2006.01) | |
| *B01J 21/08* | (2006.01) | |
| *B01J 23/40* | (2006.01) | |
| *B01J 23/46* | (2006.01) | |
| *B01J 23/70* | (2006.01) | |
| *B01J 25/02* | (2006.01) | |
| *C07C 29/132* | (2006.01) | |
| *C07C 29/141* | (2006.01) | |
| *C07C 31/20* | (2006.01) | |
| *B01J 21/06* | (2006.01) | |
| *B01J 23/30* | (2006.01) | |

(52) U.S. Cl.
CPC ............ *B01J 27/188* (2013.01); *B01J 21/08* (2013.01); *B01J 23/40* (2013.01); *B01J 23/462* (2013.01); *B01J 23/70* (2013.01); *B01J 25/02* (2013.01); *B01J 35/0006* (2013.01); *C07C 29/132* (2013.01); *C07C 29/141* (2013.01); *C07C 31/202* (2013.01); *B01J 21/063* (2013.01); *B01J 21/066* (2013.01); *B01J 23/30* (2013.01); *B01J 2231/643* (2013.01); *B01J 2523/69* (2013.01); *Y02P 20/52* (2015.11)

(58) Field of Classification Search
CPC .... C07C 29/141; C07C 31/202; B01J 27/188; B01J 25/02
See application file for complete search history.

(56) References Cited

U.S. PATENT DOCUMENTS

| | | | |
|---|---|---|---|
| 2011/0046419 A1 | 2/2011 | Zhang et al. | |
| 2011/0312487 A1 | 12/2011 | Chen et al. | |
| 2013/0289311 A1 | 10/2013 | Allgeier et al. | |

FOREIGN PATENT DOCUMENTS

| | | |
|---|---|---|
| CN | 103731258 A | 4/2014 |
| WO | 2013015955 A2 | 1/2013 |
| WO | 2014159484 A1 | 10/2014 |
| WO | 2015028398 A1 | 3/2015 |

OTHER PUBLICATIONS

International Search Report and Written Opinion received for PCT Patent Application No. PCT/EP2016/078079, dated Jan. 31, 2017, 10 pages.
Ji et al., "Direct catalytic conversion of cellulose into ethylene glycol using nickel-promoted tungsten carbide catalysts", Angewandte Chemie International Edition, Oct. 20, 2008, vol. 47, issue No. 44, pp. 8510-8513.
Ji et al., "Catalytic conversion of cellulose into ethylene glycol over supported carbide catalysts", Catalysis Today, Elsevier, NL, vol. 147, issue No. 2, Sep. 30, 2009, pp. 77-85, XP026470036.
Liu et al., "Tungsten trioxide promoted selective conversion of cellulose into propylene glycol and ethylene glycol on a ruthenium catalyst", Angewandte Chemie International Edition, Feb. 24, 2012, vol. 51, issue No. 13, pp. 3249-3253.
Zhang et al., "Kinetic study of retro-aldol condensation of glucose to glycolaldehyde with ammonium metatungstate as the catalyst", AIChE Journal, Jul. 7, 2014, vol. 60, issue No. 11, pp. 3804-3813.

*Primary Examiner* — Sikarl A Witherspoon

(57) ABSTRACT

The invention provides a catalyst system comprising: a) one or more Group 1 metal phosphotungstate-containing species; and b) one or more catalytic species suitable for hydrogenation; and a process for the preparation of monoethylene glycol from starting material comprising one or more saccharides, by contacting said starting material with hydrogen in a reactor in the presence of a solvent and said catalyst system.

12 Claims, 1 Drawing Sheet

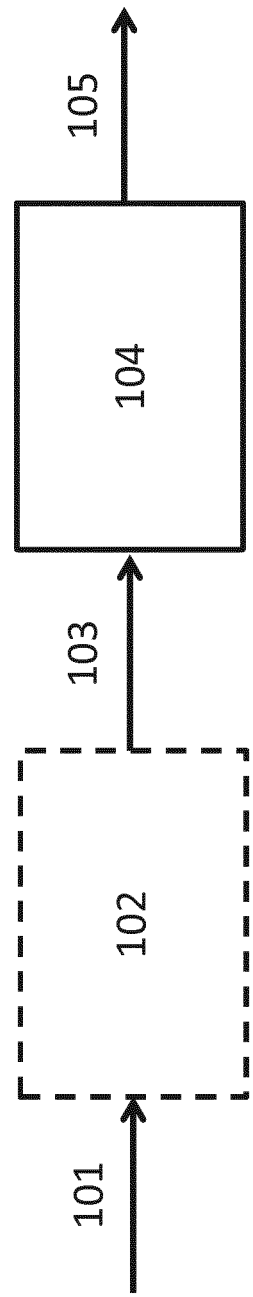

CATALYST SYSTEM AND PROCESS FOR THE PRODUCTION OF GLYCOLS

PRIORITY CLAIM

The present application is the National Stage (§ 371) of International Application No. PCT/EP2016/078079, filed 17 Nov. 2016, which claims priority from European Application No. 15195497.1, filed 19 Nov. 2015, incorporated herein by reference.

FIELD OF THE INVENTION

The present invention relates to a process for the production of glycols, in particular monoethylene glycol and monopropylene glycol from a saccharide-containing feedstock and to a catalyst system for use in said process.

BACKGROUND OF THE INVENTION

Monoethylene glycol (MEG) and monopropylene glycol (MPG) are valuable materials with a multitude of commercial applications, e.g. as heat transfer media, antifreeze, and precursors to polymers such as polyethylene terephthalate (PET).

Said glycols are currently made on an industrial scale by hydrolysis of the corresponding alkylene oxides, which are the oxidation products of ethylene and propylene, generally produced from fossil fuels.

In recent years increased efforts have been focussed on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. Current methods for the conversion of saccharides to glycols revolve around a hydrogenation/hydrogenolysis process.

Reported processes generally require a first catalytic species to perform the hydrogenolysis reaction, which is postulated to have a retro-aldol mechanism, and a second catalytic species for hydrogenation.

Processes for the conversion of cellulose to products including MEG are described in Angew. Chem. Int. Ed. 2008, 47, 8510-8513 and Catalysis Today 147 (2009), 77-85 using nickel-promoted tungsten carbide catalysts.

US 2011/0312487 A1 describes a process for generating at least one polyol from a saccharide-containing feedstock and a catalyst system for use therein, wherein said catalyst system comprises a) an unsupported component comprising a compound selected from the group consisting of a tungsten compound, a molybdenum compound and any combination thereof; and b) a supported compound comprising an active metal component selected from the group consisting of Pt, Pd, Ru, Rh, Ni, Ir, and combinations thereof on a solid catalyst support.

Examples of the unsupported catalyst component in US 2011/0312487 A1 are said to include tungstic acid ($H_2WO_4$), ammonium tungstate (($NH_4)_{10}H_2(W_2O_7)_6$), ammonium metatungstate (($NH_4)_6H_2(W_{12}O_{40}).xH_2O$), ammonium paratungstate (($NH_4)_6H_2W_{12}O_{42}).4H_2O$), and tungstate, metatungstate and paratungstate compounds comprising at least Group I or II element.

Catalyst systems tested in US 2011/0312487 A1 utilise tungstic acid, tungsten oxide ($WO_2$), phosphotungstic acid ($H_3PW_{12}O_{40}$) and ammonium metatungstate as the unsupported catalyst component in conjunction with various nickel, platinum and palladium supported catalyst components.

US 2011/03046419 A1 describes a method for producing ethylene glycol from a polyhydroxy compound such as starch, hemicellulose, glucose, sucrose, fructose and fructan in the presence of catalyst comprising a first active ingredient and a second active ingredient, the first active ingredient comprising a transition metal selected from iron, cobalt, nickel, ruthenium, rhodium, palladium, iridium, and platinum, or a mixture thereof; the second active ingredient comprising a metallic state of molybdenum and/or tungsten, or a carbide, nitride, or phosphide thereof.

Angew. Chem. Int. Ed. 2012, 51, 3249-3253 describes a process for the selective conversion of cellulose into ethylene glycol and propylene glycol in the presence of a ruthenium catalyst and tungsten trioxide ($WO_3$).

AIChE Journal, 2014, 60 (11), pp. 3804-3813 describes the retro-aldol condensation of glucose using ammonium metatungstate as catalyst.

Continuous processes for generating at least one polyol from a saccharide-containing feedstock are described in WO 2013/015955 A, CN 103731258 A and WO 2015/028398 A1.

The products of the afore-mentioned processes are typically a mixture of materials comprising MEG, MPG, 1,2-butanediol (1,2-BDO) and other by-products.

It is highly desirable to develop catalyst systems for use in the conversion of saccharide-containing feedstocks which not only give improved overall yields of the desirable MEG and MPG products, but also have increased selectivity to MEG and fewer, or more desirable, by-products being produced.

SUMMARY OF THE INVENTION

The present invention has surprisingly found that certain catalyst systems display advantageous performance in the conversion of saccharide-containing feedstocks to polyols.

Accordingly, in a first aspect of the present invention there is provided a catalyst system comprising:
a) one or more Group 1 metal phosphotungstate-containing species; and
b) one or more catalytic species suitable for hydrogenation.

In a further aspect of the present invention, there is provided a process for the preparation of monoethylene glycol from starting material comprising one or more saccharides, by contacting said starting material with hydrogen in a reactor in the presence of a solvent and said catalyst system.

BRIEF DESCRIPTION OF THE DRAWINGS

FIG. 1 is a schematic diagram of an exemplary, but non-limiting, embodiment of the process of the invention.

DETAILED DESCRIPTION OF THE INVENTION

In the present invention, there has been surprisingly found a catalyst system which gives rise to advantageous yields of ethylene glycol and propylene glycol from saccharide-containing feedstocks.

In the catalyst system of the present invention, one or more Group 1 metal phosphotungstate-containing species are present as a hydrogenolysis catalyst and there is further present one or more catalytic species which are suitable for hydrogenation.

It is required that said catalytic species have catalytic hydrogenation capabilities and are capable of catalysing the hydrogenation of material present in the reactor. The catalytic species which are suitable for hydrogenation may be present in elemental form or as one or more compounds. It is also suitable that these one or more catalytic species may be present in chemical combination with one or more other ingredients in the catalyst system.

In the one or more Group 1 metal phosphotungstate-containing species, the Group 1 metal may be conveniently selected from lithium, sodium, potassium, rubidium and caesium.

In a preferred embodiment of the present invention, the one or more Group 1 metal phosphotungstate-containing species may be selected from lithium phosphotungstate-containing species, sodium phosphotungstate-containing species, potassium phosphotungstate-containing species, caesium phosphotungstate-containing species, and mixtures thereof. More preferably, the one or more Group 1 metal phosphotungstate-containing species may be selected from sodium phosphotungstate-containing species and/or caesium phosphotungstate-containing species.

Thus, in a particularly preferred embodiment, the catalyst system of the present invention comprises one or more sodium phosphotungstate-containing species and/or caesium phosphotungstate-containing species as a hydrogenolysis catalyst and one or more catalytic species which are suitable for hydrogenation.

In the catalyst system of the present invention, the one or more catalytic species which are suitable for the hydrogenation are not limited and may be conveniently selected from one or more transition metals from Groups 8, 9 or 10 of the Periodic Table, and compounds thereof. Preferably, said catalytic species may be one or more transition metals selected from the group of cobalt, iron, platinum, palladium, ruthenium, rhodium, nickel, iridium, and compounds thereof.

In one embodiment of the present invention, the one or more catalytic species suitable for hydrogenation are solid, unsupported species. Examples of such species include Raney Ni.

In another embodiment of the present invention, the one or more catalytic species suitable for hydrogenation are in homogeneous form.

In yet another embodiment of the present invention, the one or more catalytic species suitable for hydrogenation are on one or more solid catalyst supports. The solid supports may be in the form of a powder or in the form of regular or irregular shapes such as spheres, extrudates, pills, pellets, tablets, monolithic structures. Alternatively, the solid supports may be present as surface coatings, for example, on the surfaces of tubes or heat exchangers.

Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

The Group 1 metal phosphotungstate may be present in the catalyst system in unsupported form or, alternatively, may also be present on an inert support. Examples of suitable supports include, but are not limited to, aluminas, silicas, zirconium oxide, magnesium oxide, zinc oxide, titanium oxide, carbon, activated carbon, zeolites, clays, silica alumina and mixtures thereof.

The weight ratio of the Group 1 metal phosphotungstate-containing species to the one or more catalytic species suitable for hydrogenation is preferably in the range of from 0.01:1 to 3000:1, more preferably in the range of from 0.1:1 to 100:1, on the basis of the total weight of the catalyst system.

The starting material for use in the process of the present invention comprises one or more saccharides selected from the group consisting of monosaccharides, disaccharides, oligosaccharides and polysaccharides. Examples of polysaccharides include cellulose, hemicelluloses, starch, glycogen, chitin and mixtures thereof. If the starting material comprises oligosaccharides or polysaccharides then, optionally, said starting material may be subjected to a pre-treatment before being fed to the reactor in a form that can be more conveniently converted in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the starting material for use in the process of the present invention comprises one or more saccharides selected from the group consisting of glucose, sucrose and starch. Said saccharides are suitably present as a solution, a suspension or a slurry in solvent.

The solvent present in the reactor is not limited and may be conveniently selected from water, $C_1$ to $C_6$ alcohols, ethers, and other suitable organic compounds, and mixtures thereof. Preferably, the solvent is water. If the starting material is provided to the reactor as a solution, suspension or slurry in a solvent, said solvent is also conveniently selected from water, $C_1$ to $C_6$ alcohols, ethers, and other suitable organic compounds, and mixtures thereof. Preferably, both solvents are the same. More preferably, both solvents comprise water. Most preferably, both solvents are water.

In the process of the present invention, the one or more Group 1 metal phosphotungstate-containing species are typically employed in the catalyst system in an amount in the range of from 0.001 to 10 wt. %, more preferably in an amount in the range of from 0.001 to 6 wt. %, and most preferably in an amount in the range of from 0.001 to 3 wt. %, based on the total weight of the reaction mixture.

By "reaction mixture" in the present invention, is meant the total weight of the starting material, catalyst system and solvent present in the reactor.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. It is particularly preferred that the reactor temperature is in the range of from 130 to 300° C., more preferably in the range of from 150 to 270° C., and most preferably in the range of from 190 to 250° C. Preferably, the reactor is heated to a temperature within these limits before addition of any starting material and is maintained at such a temperature until all reaction is complete.

The pressure in the reactor is generally at least 1 MPa, preferably at least 2 MPa, more preferably at least 3 MPa. The pressure in the reactor is generally at most 25 MPa, more preferably at most 20 MPa, more preferably at most 18 MPa. Preferably, the reactor is pressurised to a pressure within these limits by addition of hydrogen before addition of any starting material and is maintained at such a pressure until all reaction is complete. This can be achieved by subsequent addition of hydrogen. The process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents. It may also be suitable to add further hydrogen to the reactor as the reaction proceeds.

The reactor in the present invention may be any suitable reactor known in the art.

The process may be carried out as a batch process or as a continuous flow process.

In one embodiment of the invention, the process is a batch process. In such a process, the reactor may be loaded with the catalyst system, solvent and one or more saccharides, and the reactor may then be pressurised with hydrogen at room temperature, sealed and heated to the reaction temperature.

In semi-continuous processes, further portions of starting material may be added to the reactor over time until the total concentration of saccharide in the solvent in the reactor is at least 5 wt. %.

"Total concentration" as used herein refers to the concentration calculated as a weight percentage of the total amount of saccharide added in the total amount of solvent present in the reactor. The total amount of saccharide added corresponds to the sum total of the amount of saccharide added in the first portion and all further portions, if any. The total amount of solvent in the reactor includes any solvent already present in the reactor as well as any solvent present in the slurry, solution or suspension of the starting material. Preferably, further portions of starting material are added to the reactor over time until the total concentration of one or more saccharides in the solvent in the reactor is at least 5 wt. %, more preferably at least 8 wt. %, even more preferably at least 10 wt. %. Suitably, the total concentration of one or more saccharides in the solvent is no higher than 50 wt. %, preferably no higher than 40 wt. %.

In embodiments of the invention, addition of further portions of starting material may occur in a continuous manner or the portions may be added in a discontinuous manner with time elapsing between the end of the addition of one portion and the start of the addition of the next portion. In the embodiments of the invention wherein the portions are added in a discontinuous manner, the number and size of each portion will be dependent on the scale of the reactor. Preferably, the total number of portions including the first portion is no less than 5, more preferably no less than 8, even more preferably no less than 10. The amount of time over which each portion is added and the time to be elapsed between the end of the addition of one portion and the start of the addition of the next portion will also depend on the scale of the reactor. Preferably, the time to be elapsed between the end of the addition of one portion and the start of the addition of the next portion will be greater than the amount of time over which each portion is added.

In embodiments of the invention wherein the process is a batch process, after addition of all of the portions of the starting material, the reaction may then be allowed to proceed to completion for a further period of time. The reaction product will then be removed from the reactor.

In embodiments of the invention wherein the process is carried out as a continuous flow process, after initial loading of some or all of the catalysts and, optionally, solvent, the reactor is heated and pressurised with hydrogen and then the first portion of starting material is introduced into the reactor. Further portions of starting material are then provided to the reactor. Reaction product is removed from the reactor in a continuous manner. In some embodiments of the invention, catalysts may be added in a continuous fashion.

In embodiments of the present invention, the starting material is suitably a saccharide feedstock comprising at least 1 wt. % saccharide as a solution, suspension or slurry in a solvent. Preferably, said saccharide feedstock comprises at least 2 wt. %, more preferably at least 5 wt. %, even more preferably at least 10 wt. %, most preferably at least 20 wt. % saccharide in a solvent. Suitably, the saccharide feedstock contains no more than 50 wt. %, preferably no more than 40 wt. % saccharide in a solvent.

The weight ratio of catalyst system to saccharides in the starting material is suitably in the range of from 1:100 to 1:10000.

FIG. 1 is a schematic diagram of an exemplary, but non-limiting, embodiment of the process of the invention. A feed 101 comprising polysaccharides and solvent is provided to a pre-treatment unit 102 to convert it mainly into glucose, sucrose and/or starch in solvent to form feed 103. The pre-treatment unit 102 may consist of multiple pre-treatment units performing the same or different pre-treatment functions. Pre-treatment is an optional step in case the feed is polysaccharide. Feed 103 is then fed to the main reactor 104 where it undergoes hydrogenation/hydrogenolysis in the presence of the catalyst system to produce a product stream 105 comprising MEG.

The process of the present invention is not limited to any particular reactor or flow configurations, and those depicted in FIG. 1 are merely exemplary. Furthermore, the sequence in which various feed components are introduced into the process and their respective points of introduction, as well as the flow connections, may be varied from that depicted in FIG. 1.

The invention is further illustrated by the following Examples.

EXAMPLES 75 ml Hastelloy C batch autoclaves, with magnetic stir bars, were used to screen various conditions, catalyst systems and feedstocks.

In typical experiments, known weights of catalysts and feedstocks were added to the autoclaves along with 30 ml of the solvent (typically water).

If the catalysts or feedstocks were present as slurries or solutions, the total volume of those as well as the solvent was kept at 30 ml.

Example 1

Methodology

In Example 1, 0.3 g of glucose was dissolved in 30 ml of water. Catalysts were also added to the solution. The loaded autoclave was then purged three times with nitrogen, followed by hydrogen purge.

The hydrogen pressure was then raised to 2000 psig or ~14 MPa of hydrogen and the autoclave was sealed and left stirring overnight to do a leak test.

The next morning the autoclave was de-pressurised to the target hydrogen pressure (1450 psig or 10.1 MPa) at room temperature, and closed. Next, the temperature was ramped to the target run temperature (195 deg C.) either as a fast ramp or in steps.

In Example 1, there was a fast ramp to temperature. The autoclave was held at the target temperature for known durations of time (75 min), while both the temperature and pressure were monitored. After the required run time had elapsed, the heating was stopped, and the reactor was cooled down to room temperature, de-pressurised, purged with nitrogen and then opened.

The contents of the autoclave were then analyzed via Gas Chromatography (GC) or High Pressure Liquid Chromatography (HPLC) after being filtered. The yields of the various components were measured as wt. % basis the total saccharide loaded.

Table 1 provides details on the catalyst systems tested in Example 1. Catalyst systems A to D are comparative in nature and are known in the art as suitable tungsten catalyst systems for the conversion of saccharide-containing feedstocks to monoethylene glycol. Catalyst systems E to H are according to the present invention.

TABLE 1

| Catalyst System | Hydrogenolysis Catalyst (a) | | Hydrogenation Catalyst (b) | | Ratio (a):(b) |
|---|---|---|---|---|---|
| | Component | Amount g | Component | Amount g | |
| A (Comp) | Tungstic acid ($H_2WO_4$) | 0.0672 | 1% Ru on $SiO_2$ | 0.045 | 1.5 |
| B (Comp) | 10% W, 2% Mo on $ZrO_2$ | 0.025 | 1% Ru on $SiO_2$ | 0.025 | 1.0 |
| C (Comp) | 10% W on $TiO_2$ | 0.025 | 1% Ru on $SiO_2$ | 0.025 | 1.0 |
| D (Comp) | 10% W on $TiO_2$ | 0.025 | Raney Ni 2800 | 0.008 | 3.1 |
| E | Sodium phosphotungstate | 0.015 | 1% Ru on $SiO_2$ | 0.045 | 0.3 |
| F | Sodium phosphotungstate | 0.045 | Raney Ni 2800 | 0.009 | 5.0 |
| G | Caesium phosphotungstate | 0.017 | 1% Ru on $SiO_2$ | 0.045 | 0.4 |
| H | Caesium phosphotungstate | 0.017 | Raney Ni 2800 | 0.007 | 2.4 |

Discussion

It is apparent from the results in Table 2 that Catalyst Systems E to H, according to the present invention not only give the highest yields of monoethylene glycol but also the largest total yield of monoethylene glycol, monopropylene glycol and hydroxyacetone.

Surprisingly, use of Catalyst System E and G results in a very high C2:C3 ratio (MEG:(MPG+HA)).

Further Catalyst Systems G and H, according to the present invention, give marginally higher yields of monoethylene glycol relative to Catalyst Systems E and F, also according to the present invention.

TABLE 2

| Catalyst System | MEG wt. % | MPG wt. % | HA* wt. % | 1,2-BDO** wt. % | 1H2BO*** wt. % | MEG: (MPG + HA) |
|---|---|---|---|---|---|---|
| A (Comp) | 19.3 | 2.6 | 10.2 | 2.8 | 14.7 | 1.5 |
| B (Comp) | 12.0 | 0.0 | 9.9 | 2.2 | 13.8 | 1.2 |
| C (Comp) | 33.9 | 4.8 | 2.9 | 1.9 | 2.7 | 4.5 |
| D (Comp) | 15.5 | 2.1 | 0.6 | 1.3 | 0.7 | 5.8 |
| E | 38.1 | 3.9 | 1.4 | 1.7 | 2.1 | 7.2 |
| F | 36.7 | 4.9 | 2.6 | 3.4 | 3.9 | 4.9 |
| G | 41.2 | 2.5 | 2.7 | 1.4 | 4.4 | 7.8 |
| H | 39.6 | 5.6 | 2.3 | 4.2 | 3.9 | 5.0 |

*hydroxyacetone
**1,2-butanediol
***1-hydroxy 2-butanone

Example 2

Methodology

The same methodology as described in Example 1 was used except 0.3 g glucose equivalence of various saccharides were used.

0.045 g of sodium phosphotungstate and 0.02 g of Raney Ni 2800 were used as the catalyst system (Catalyst System I).

Two different corn starches were used as the saccharide-containing feedstock in Experiment Runs 1 and 2 and the reaction temperature was 195 deg C. When using cellulose as the feedstock, the run temperature was 245 deg C.

Table 3 provides details of the different saccharides used and the experimental temperature.

TABLE 3

| Experiment Run | Saccharide-containing feedstock | Reaction Temperature deg C. |
|---|---|---|
| 1 | Corn starch 1 | 195 |
| 2 | Corn starch 2 | 195 |
| 3 | Cellulose | 245 |

Results

Table 4 presents the results of Example 2.

TABLE 4

| Experiment Run | MEG wt. % | MPG wt. % | HA* wt. % | 1,2-BDO** wt. % | 1H2BO*** wt. % | MEG: (MPG + HA) |
|---|---|---|---|---|---|---|
| 1 | 43.0 | 5.9 | 3.2 | 4.3 | 4.3 | 4.8 |
| 2 | 41.1 | 5.5 | 0.7 | 4.3 | 0.9 | 6.6 |
| 3 | 53.7 | 5.7 | 0.0 | 3.5 | 0.9 | 9.4 |

*hydroxyacetone
**1,2-butanediol
***1-hydroxy 2-butanone

Discussion

It is apparent from Table 4 that Catalyst System I is an effective catalyst system for a variety of saccharide sources and high yields of MEG as well as high total yields of MEG, MPG and HA are obtained.

That which is claimed is:

1. A catalyst system comprising:
   a) one or more sodium phosphotungstate-containing species; and
   b) one or more catalytic species suitable for hydrogenation.

2. The catalyst system according to claim 1, wherein the one or more catalytic species suitable for hydrogenation are selected from one or more transition metals from Groups 8, 9 or 10 of the Periodic Table, and compounds thereof.

3. The catalyst system according to claim 1, wherein the one or more catalytic species suitable for hydrogenation are selected from one or more transition metals selected from the group of cobalt, iron, platinum, palladium, ruthenium, rhodium, nickel, iridium, and compounds thereof.

4. The catalyst system according to claim 1, wherein the one or more catalytic species suitable for hydrogenation are solid, unsupported species.

5. The catalyst system according to claim 1, wherein the one or more sodium phosphotungstate-containing species and/or the one or more catalytic species suitable for hydrogenation are on solid catalyst supports.

6. The catalyst system according to claim 5, wherein the solid catalyst supports are selected from aluminas, silicas, zirconium oxide, magnesium oxide, zinc oxide, titanium oxide, carbon, activated carbon, zeolites, clays, silica alumina and mixtures thereof.

7. The catalyst system according to claim 1, wherein the weight ratio of the one or more sodium metal phosphotungstate-containing species to the one or more catalytic species suitable for hydrogenation is in the range of from 0.01:1 to 3000:1, on the basis of the total weight of the catalyst system.

8. A process for the preparation of monoethylene glycol from starting material comprising one or more saccharides, by contacting said starting material with hydrogen in a reactor in the presence of a solvent and the catalyst system according to claim 1.

9. The process according to claim 8, wherein the saccharides are selected from the group consisting of monosaccharides, disaccharides, oligosaccharides and polysaccharides.

10. The process according to claim 8, wherein the one or more sodium phosphotungstate-containing species are present in an amount in the range of from 0.001 to 10 wt. %, based on the total weight of the reaction mixture.

11. The process according to claim 8, wherein the reactor temperature is in the range of from 130 to 300° C.

12. The process according to claim 8, wherein the reactor pressure is in the range of from at least 1 to at most 25 MPa.

\* \* \* \* \*